(12) United States Patent
Moberg

(10) Patent No.: US 8,012,144 B2
(45) Date of Patent: Sep. 6, 2011

(54) ELONGATE MEDICAL DEVICE HAVING AN INTERFERENCE FIT PACKAGING MEMBER

(75) Inventor: John Moberg, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1682 days.

(21) Appl. No.: 10/667,936

(22) Filed: Sep. 22, 2003

(65) Prior Publication Data

US 2005/0061697 A1    Mar. 24, 2005

(51) Int. Cl.
*A61M 39/00* (2006.01)
*A61M 25/16* (2006.01)
*B65D 69/00* (2006.01)
*B65D 71/00* (2006.01)

(52) U.S. Cl. .................. 604/533; 206/571

(58) Field of Classification Search .......... 206/363–365, 206/571, 438, 210; 604/533, 539, 103.05, 604/264, 262, 535, 164.08; 220/796, 805, 220/806; 215/387, 388
See application file for complete search history.

(56) References Cited

U.S. PATENT DOCUMENTS

| | | | |
|---|---|---|---|
| 2,185,741 A | 1/1940 | Sorg et al. | |
| RE25,788 E | 6/1965 | Sheridan | |
| 3,307,552 A * | 3/1967 | Strawn | 604/256 |
| 3,318,335 A | 5/1967 | Heller | |
| 3,348,544 A | 10/1967 | Braun | |
| 3,470,869 A | 10/1969 | Fenton et al. | |
| 3,720,210 A | 3/1973 | Diettrich | |
| 3,725,522 A | 4/1973 | Sheridan et al. | |
| 3,752,510 A | 8/1973 | Windischman et al. | |
| 3,861,972 A | 1/1975 | Glover et al. | |
| 3,865,666 A | 2/1975 | Shoney | |
| 3,873,391 A | 3/1975 | Plauka et al. | |
| 3,914,002 A | 10/1975 | Berliner et al. | |
| 3,950,052 A | 4/1976 | Walter et al. | |
| 3,959,429 A | 5/1976 | Benning | |
| 3,985,601 A | 10/1976 | Panagrossi | |
| 3,989,571 A | 11/1976 | Harautuneian | |
| 4,085,185 A | 4/1978 | Adair | |
| 4,093,484 A | 6/1978 | Harrison et al. | |
| 4,130,304 A * | 12/1978 | Hebard | 285/123.14 |
| 4,154,244 A | 5/1979 | Becker et al. | |
| 4,171,943 A | 10/1979 | Tschanz et al. | |
| 4,191,185 A | 3/1980 | Lemieux | |
| 4,198,983 A | 4/1980 | Becker et al. | |
| 4,207,900 A | 6/1980 | Patel et al. | |
| 4,210,478 A | 7/1980 | Shoney | |
| 4,247,968 A | 2/1981 | Moertel | |
| 4,284,459 A | 8/1981 | Patel et al. | |
| 4,328,056 A | 5/1982 | Snooks | |

(Continued)

FOREIGN PATENT DOCUMENTS

EP    0 782 868 A1    7/1997

(Continued)

*Primary Examiner* — Jila M Mohandesi
*Assistant Examiner* — Melissa L Lalli
(74) *Attorney, Agent, or Firm* — Seager, Tufte & Wickhem, LLC

(57) ABSTRACT

An elongate medical device including a hub assembly located at the proximal end. The hub assembly includes an interference fit member disposed about a portion of the hub assembly, whereby the interference fit member is configured to form an interference fit with the inner surface of a tubular packaging tube when the elongate medical device is placed in the packaging tube.

17 Claims, 6 Drawing Sheets

U.S. PATENT DOCUMENTS

| | | | |
|---|---|---|---|
| 4,354,495 A | 10/1982 | Bodicky | |
| 4,489,961 A | 12/1984 | Laidig | |
| 4,509,877 A | 4/1985 | Sobin et al. | |
| 4,511,163 A | 4/1985 | Harris et al. | |
| 4,607,746 A | 8/1986 | Stinnette | |
| 4,692,150 A * | 9/1987 | Cianci et al. | 604/111 |
| 4,903,826 A | 2/1990 | Pearce | |
| 5,014,939 A | 5/1991 | Kraus et al. | |
| 5,031,775 A | 7/1991 | Kane | |
| 5,125,906 A | 6/1992 | Fleck | |
| 5,181,913 A | 1/1993 | Erlich | |
| 5,217,114 A | 6/1993 | Gadberry et al. | |
| 5,309,604 A | 5/1994 | Poulsen | |
| 5,344,011 A | 9/1994 | DiBernardo et al. | |
| 5,364,355 A | 11/1994 | Alden et al. | |
| 5,366,444 A | 11/1994 | Martin | |
| 5,372,592 A | 12/1994 | Gambale | |
| 5,419,764 A * | 5/1995 | Roll | 604/95.04 |
| 5,531,701 A * | 7/1996 | Luther | 604/165.04 |
| 5,533,974 A * | 7/1996 | Gaba | 604/110 |
| 5,569,222 A * | 10/1996 | Haselhorst et al. | 604/533 |
| 5,607,055 A | 3/1997 | Bettinger | |
| 5,749,603 A | 5/1998 | Mann | |
| 5,755,225 A | 5/1998 | Hutson | |
| 5,830,401 A | 11/1998 | Prichard et al. | |
| 5,941,849 A * | 8/1999 | Amos et al. | 604/95.04 |
| 5,944,701 A | 8/1999 | Dubrul | |
| 5,954,707 A | 9/1999 | Kanesaka et al. | |
| 5,976,107 A * | 11/1999 | Mertens et al. | 604/164.13 |
| 6,042,577 A * | 3/2000 | Chu et al. | 604/523 |
| 6,053,313 A | 4/2000 | Farrell et al. | |
| 6,068,121 A | 5/2000 | McGlinch | |
| 6,068,622 A | 5/2000 | Sater et al. | |
| 6,228,073 B1 | 5/2001 | Noone et al. | |
| 6,231,564 B1 | 5/2001 | Gambale | |
| 6,273,404 B1 | 8/2001 | Holman et al. | |
| 6,405,414 B1 | 6/2002 | Byrnes et al. | |
| 6,551,273 B1 | 4/2003 | Olson et al. | |
| 7,214,220 B2 * | 5/2007 | McGlinch et al. | 604/533 |
| 2001/0037954 A1 | 11/2001 | Schmidt et al. | |
| 2003/0060803 A1 | 3/2003 | McGlinch et al. | |
| 2003/0125713 A1 | 7/2003 | McGlinch et al. | |

FOREIGN PATENT DOCUMENTS

| | | |
|---|---|---|
| FR | 2092970 | 1/1972 |
| WO | WO 98/18515 A1 | 5/1998 |
| WO | WO 03/026535 A2 | 4/2003 |

* cited by examiner

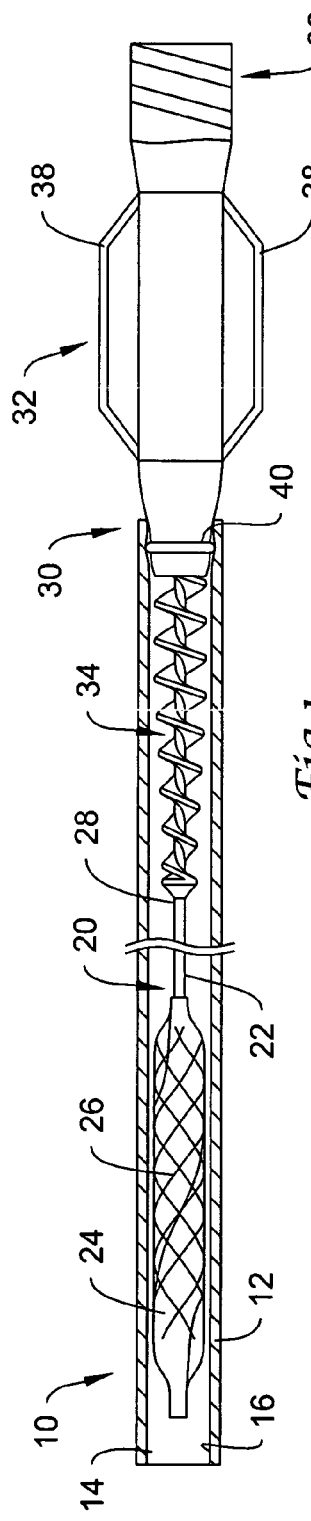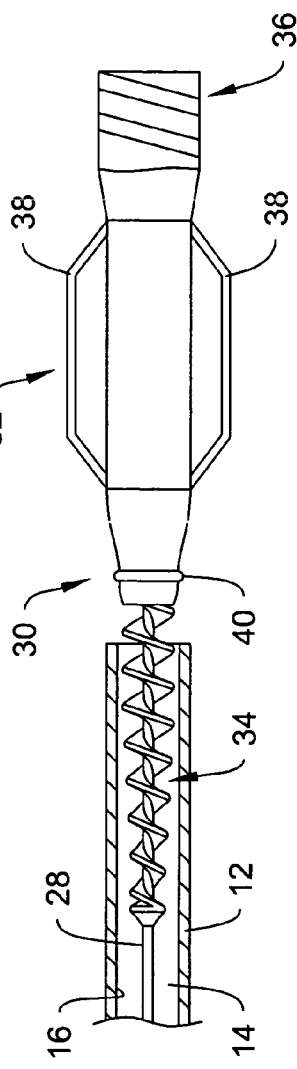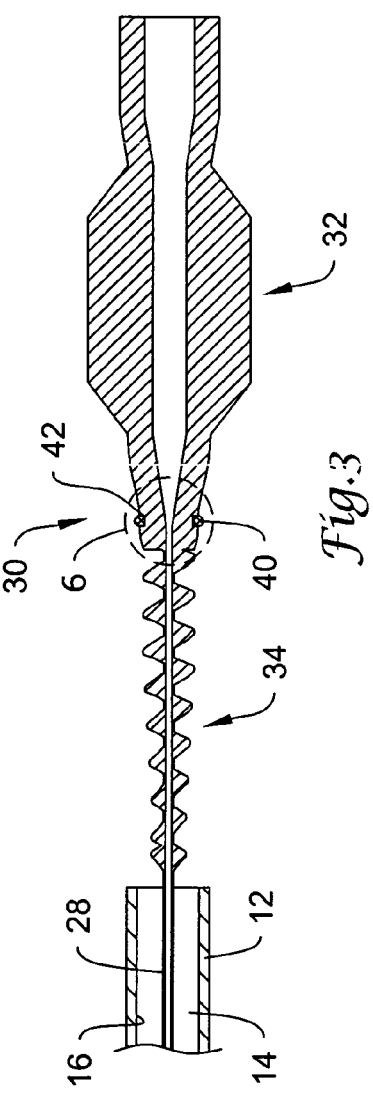

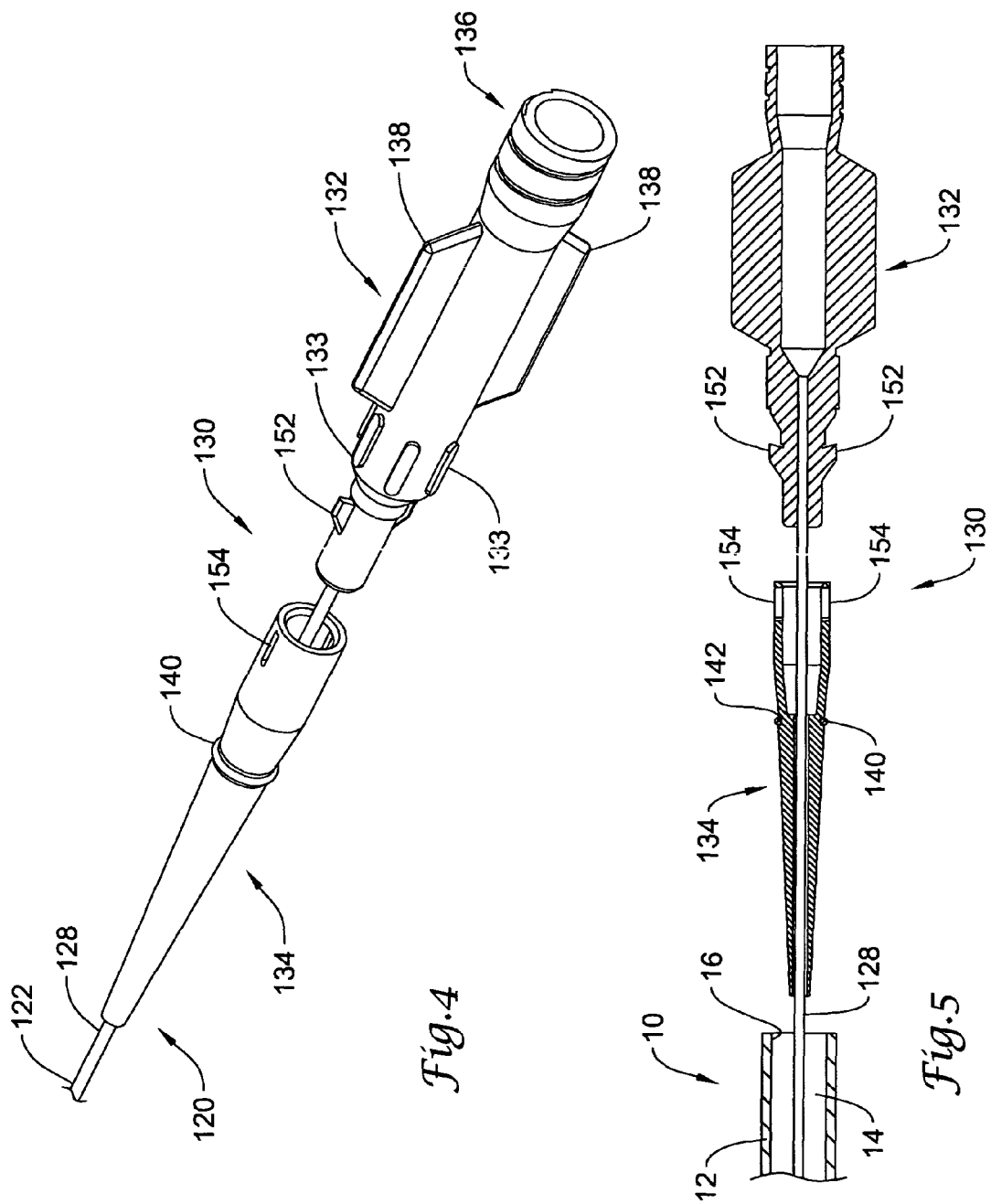

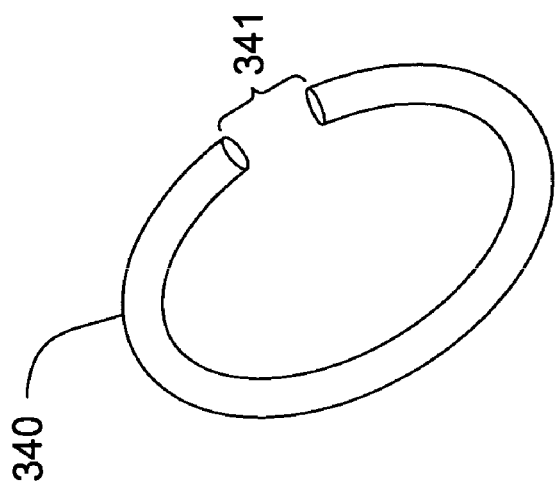
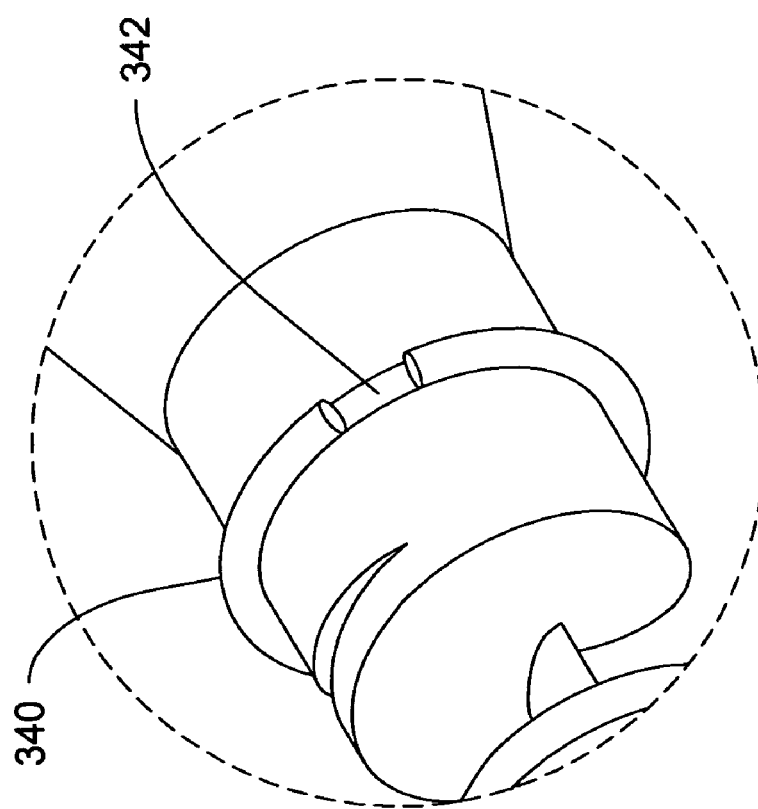

ELONGATE MEDICAL DEVICE HAVING AN INTERFERENCE FIT PACKAGING MEMBER

FIELD OF THE INVENTION

The invention generally relates to medical devices and packaging thereof. More specifically, the invention relates to the packaging of elongate medical devices, in particular, catheters, in a generally tubular member.

BACKGROUND OF THE INVENTION

Elongate medical devices can be packaged in carrier tubes. A carrier tube provides a way to package and handle an elongated medical device prior to use, which prevents damage and generally maintains the device in a controlled environment. A medical device placed slidably in a carrier tube can have a tendency to fall out of the tube, particularly since the larger/heavier manifold remains outside the end of the tube. Unintentional removal of a medical device may contaminate or damage the device, therefore rendering the medical device unusable for a medical procedure. As such, there is an ongoing need to provide improved devices and packaging techniques to reduce this potential for damage or contamination.

SUMMARY OF THE INVENTION

Several embodiments of the present invention are contemplated. In one embodiment of the invention, for example, provides an elongate medical device having a hub assembly located at a proximal end. The hub assembly includes a manifold and a strain relief member integrally formed with the manifold. An interference fit member is disposed about a distal portion of the manifold. The interference fit member is configured to form an interference fit with the inner surface of a packaging tube when the elongate medical device and the interference fit member are disposed in the lumen of the packaging tube.

In another embodiment of the invention, a hub assembly is provided at the proximal portion of the elongate medical device. The hub assembly includes a manifold and a strain relief member fixed to the manifold. An interference fit member is disposed about a portion of the strain relief member. The interference fit member is configured to provide an interference fit with the inner wall of a generally tubular member when the portion of the strain relief member including the interference fit member is disposed within the lumen of the generally tubular member.

In yet another embodiment of the invention, an elongate medical device comprising a hub assembly located near the proximal end is configured to be securely disposed within a packaging tube. A circumferential channel is formed in a distal portion of the hub assembly. A circumferential interference fit member is disposed about the circumferential channel, wherein the circumferential channel retains the interference fit member. The circumferential interference fit member provides a raised surface for engaging the inner surface of a packaging tube, whereby the interference fit member provides an interference fit with the inner surface of the packaging tube when the interference fit member is disposed in the lumen of the packaging tube. The interference fit member prevents the elongate medical device from prematurely disengaging from the packaging tube.

BRIEF DESCRIPTION OF THE DRAWINGS

FIG. 1 is a partially cross-sectioned plan view of an elongate medical device retained in a packaging tube with an interference fit member;

FIG. 2 is a partially cross-sectioned plan view of an elongate medical device as in FIG. 1, wherein the interference fit member is disengaged from the packaging tube;

FIG. 3 is a cross-sectional view of the manifold portion of the elongate medical device in FIG. 1;

FIG. 4 is a partial perspective view of an alternative embodiment of an elongate medical device showing a strain relief prior to attachment to the hub;

FIG. 5 is cross-sectional view of the elongate medical device in FIG. 4;

FIG. 7A is an enlarged perspective view of the portion of the elongate medical device in FIG. 7 having an interference fit member; and FIG. 7B is an enlarged perspective view of the interference fit member according to FIG. 7.

DETAILED DESCRIPTION OF THE DRAWINGS

Figure 6A:
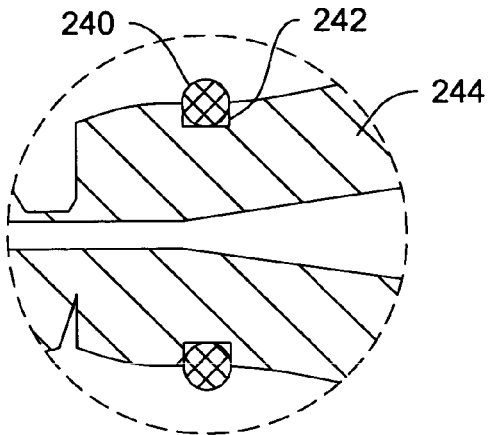
FIGS. 6A-6J are enlarged cross-sectional views of alternative embodiments of interference fit members and arrangements provided with an elongate medical device.

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates a partially cross-sectioned plan view of a carrier tube and an elongate medical device disposed therein. By way of example, not limitation, the carrier tube is shown to be a packaging tube 10 having a packaging tube lumen 14 defined by a packaging tube wall 12 having an inner surface 16. The packaging tube lumen 14 can be sized to accommodate substantially the entire length of the elongate medical device 20 therein. The packaging tube lumen 14 can have an open proximal end and an open or closed distal end. As illustrated, the packaging tube is generally straight. However, it is recognized that the length of tubing can be configured in any shape desired, such as circles of increasing diameter to fix a particular packaging configuration.

The packaging tube 10 can be formed utilizing conventional materials, dimensions and techniques. For example, the packaging tube 10 can be formed of an extruded polymer including a blend of 50% polyolefin copolymer available under the trade name SURLYN and 50% high density polyethylene, having an inside diameter ranging from about 0.10 to about 0.30 inches (about 2.5 to about 7.6 millimeters), a wall thickness ranging from about 0.002 to about 0.020 inches (about 0.05 to about 0.5 millimeters), and a length ranging from about 12 to about 72 inches (about 30 to about 180 centimeters). Other suitable polymers for the packaging tube 10 include thermoplastics such as fluoropolymers (PTFE, FEP, PFA, CTFE), nylons, phenylene oxides, polyesters, polyethylenes, polypropylene, polyurethanes and combinations thereof.

The elongate medical device 20 can be removably disposed in the lumen 14 of the packaging tube 10. The elongate medical device 20 generically refers to a wide variety of elongate medical devices including intravascular devices such as catheters and guide wires. For example, the elongate medical device 20 can include a balloon catheter, a guide catheter, a diagnostic catheter, a guidewire, a drug delivery catheter, an atherectomy catheter, a tubular sheath or a stent delivery catheter. However, the elongate medical device 20 may also include tracheal tubes, gastrostomy tubes, intravenous (IV) tubing, or other elongate devices used during a medical procedure.

For purposes of illustration only, elongate medical device 20 is shown in the form of an intravascular balloon catheter 20 having an elongate shaft 22, a distally mounted balloon 24 and a stent 26 disposed thereon. A proximal portion 28 of the elongate shaft 22 is connected to a hub assembly 30.

The hub assembly 30 includes a manifold 32 and a strain relief member 34. The proximal portion 28 of the elongate shaft 22 may extend through the strain relief member 34 and into the manifold 32. Alternatively, the hub assembly, or a portion thereof, may provide a shaft extension connected to the elongate shaft 22. The hub assembly 30 can be adhesively or thermally bonded to the proximal shaft portion 28. Alternatively, the proximal portion 28 of the elongate shaft 22 can be connected to the hub assembly 30 by an insert molding technique. As a further alternative, the hub assembly 30 can be removably connected to the proximal shaft portion 28 utilizing a releasable compression fitting or other mechanical means.

The manifold 32 and the strain relief member 34 can be a multi-piece construction, a two-piece construction, or a one-piece construction as shown. Examples of one-piece and two-piece constructions are described in U.S. Pat. No. 6,273,404 to Holman et al., the entire disclosure of which is incorporated herein by reference. In one-piece constructions, the manifold 32 and the strain relief member 34 can be formed of the same material, such as polycarbonate. Other moldable polymeric materials having sufficient impact resistance and chemical resistance can be utilized as well. In two-piece constructions, the manifold 32 and the strain relief member 34 can be formed of two different materials. For example, the manifold 32 can be formed of polycarbonate, and the strain relief member 34 can be formed of a relatively less rigid polymer such as polyurethane available under the trade name PELLETHANE. In multi-piece constructions, multiple materials may be used for different portions of the hub assembly 30 for their superior characteristics and compatibility. Alternative materials may be used for portions of the hub assembly 30, and the invention is not intended to be limited by the materials used for the hub assembly 30.

The strain relief member 34 reduces the tendency of the proximal shaft portion 28 to kink just distal of the manifold 32. The manifold 32 can be relatively stiff and rigid, whereas the shaft 22 can be relatively flexible, which can create a stress concentration point therebetween, absent the strain relief member 34. Thus, the strain relief member 34 provides a gradual transition in stiffness between the manifold 32 and the proximal shaft portion 28. In this particular embodiment, the strain relief member 34 has a helical shape and a gradual reduction in profile to provide such a transition in stiffness. The strain relief member 34 may be formed of various shapes, such as an elongated conical member.

In this particular embodiment, the manifold 32 includes a single port fluid connector 36 for connection to an ancillary device such as an inflation device (not shown). The manifold 32 can incorporate more than one connector 36, or no connector at all, depending on the type of elongated medical device 20 utilized. For example, an otherwise conventional guide wire may not require a fluid connector 36, whereas an otherwise conventional over-the-wire (OTW) type balloon catheter may require two port connections.

Also in this particular embodiment, the hub assembly 30 includes a pair of wings 38 to facilitate easier handling and manipulation of the device 20. The particular shape and number of wings 38 can vary, depending on the manipulation requirements of the device 20 and design choices. In some instances, wings 38 may not be necessary or desirable.

The hub assembly 30 includes an interference fit member (IFM) 40 disposed about a distal portion of the manifold 32, proximal of the strain relief member 34. The IFM 40 can be disposed about any portion of the hub assembly 30, to any portion of the proximal shaft 28, or to any portion of the strain relief member 34. The IFM 40 may be configured to provide an interference fit with the packaging tube 10. The IFM 40 can form an interference fit with any portion of the pacakging tube 10, such as the inside surface 16 of the packaging tube wall 12 as shown in FIG. 1.

The packaging tube wall 12 and/or the IFM 40 can have sufficient compressibility to deform and thereby permit the IFM 40 to enter into the packaging tube lumen 14 despite a nominal difference in size. The interference fit between the IFM 40 and the packaging tube 10 establishes sufficient friction to resist gravitational and handling forces that can otherwise cause the device 20 to fall out of the packaging tube 10 prematurely. The friction created by the interference fit can also be sufficiently small to permit easy removal of the device 20 from the packaging tube 10 when desired as shown in FIG. 2. The IFM 40 and/or packaging tube 10 may be sized in order to provide sufficient interference force in order to retain the medical device 20 in packaging tube 10 until removal of medical device 20 is desired.

The IFM 40 can be sized and shaped to be fully or partially disposed inside the packaging tube lumen 14. By extending the IFM 40 into the packaging tube lumen 14 a distance from the proximal end of the packaging tube 10, the IFM 40 is less likely to be accidentally dislodged by rough handling or the like. To this end, the IFM 40 can establish a contact surface area with the inside surface of the packaging tube wall 14 that is distal of the proximal end of the packaging tube 10.

In the embodiment illustrated in FIGS. 1-3, the IFM 40 includes a circumferential ring. The IFM 40 may be made from a number of materials, and the invention is not limited by the material of the IFM 40. For example, the IFM 40 may comprise an elastomer, silicone, thermal plastic rubber, latex, polymer, or oil-based material. It is desirable that the IFM 40 comprises a medical grade material. It is preferred that the IFM 40 includes a material that is readily deformable and/or more compressible than the portion of the hub assembly 30 adjacent the IFM 40. Therefore, the shape of IFM 40 may be altered when inserted in the packaging tube 10 to provide an interference fit without damaging the shape or integrity of the elongate medical device 20. The IFM 40 may be a preformed component such as an O-ring or a lip seal, or the IFM 40 may be a bead placed on at least a portion of the hub assembly 30 and adhered to the hub assembly 30. The bead may be a silicone or latex caulk or a number of other elastomeric materials. The bead may be adhered to the hub assembly 30 by an adhesive, or the bead may be adhered by chemical or thermal bonding of the bead in contact with the hub assembly 30. It is contemplated that the bead may not be adhered to the hub assembly 30, but may be mechanically held in place by a circumferential channel or indentation on the hub assembly 30.

As shown best in FIG. 3, the hub assembly 30 may include a channel 42. The channel 42 is preferably circumferential about a portion of the hub assembly 30. However, the channel 42 may be substantially helical or segmented. The channel may be molded into the hub assembly 30, or may be added in a later manufacturing process. The channel 42 may be a groove, a V-notch, a concave channel, a flat-bottomed channel, or other recessed area or indentation. The IFM 40 is disposed about at least a portion of the channel 42, wherein the channel 42 helps retain the IFM 40. Preferably, the IFM 40 is sized in order to provide a raised surface above the outer surface of the hub assembly 30 adjacent the channel 42. The raised surface portion of the IFM 40 may be sized to provide an interference fit with the inner surface 16 of the packaging tube 10 in order to retain the elongate medical device 20 in the packaging tube 10.

FIG. 4 illustrates a partial perspective view of an alternative embodiment of an elongate medical device 120. The elongate medical device 120 includes an elongate shaft 122 and a hub assembly 130 connected to a proximal portion 128 of the elongate shaft 122. The hub assembly 130 includes a manifold 132 having a distal portion fixed to a strain relief member 134. The portions of the hub assembly 130 may be substantially similar to those of hub assembly 30 or may contain any variations disclosed herein. The manifold 132 includes wings 138 and fluid port 136 similar to those of manifold 32. The manifold 132 also includes grips 133 disposed about a distal portion of the manifold 132 proximal the strain relief member 134. Grips 133 may facilitate operation and manipulation of the elongate medical device 120.

The strain relief member 134 is connected to the manifold 132. The strain relief member 134 may be connected to the manifold 132 by mechanical means, chemical bonding, thermal bonding, compression fit, or other suitable means. As better shown in FIG. 5, manifold 132 may include a plurality of tabs 152 configured to engage with notches 154 in the strain relief member 134. Engagement of the tabs 152 in notches 154 provides a snap-fit securely fixing the strain relief member 134 to the manifold 132. It is contemplated that the strain relief member 134 may include tabs 152, and the manifold 132 may include notches 154. Other suitable locking means are within the scope of the invention.

IFM 140 is disposed about a portion of the strain relief member 134. The IFM 140 may be substantially similar to IFM 40 described above. Preferably, IFM 140 provides a raised surface around at least a portion of the strain relief member 134 in order to contact the inner surface 16 of the packaging tube 10. As shown in FIG. 5, the strain relief member may include channel 142 for receiving at least a portion of the IFM 140. The channel 142 may help retain IFM 140 in a proper location. The channel 142 may be molded in the strain relief member 134 or may be added during a later manufacturing process. The channel 142 may be of a variety of shapes and sizes, and the invention is not intended to be limited by the type or shape of channel used. As shown in FIG. 5, the channel 142 and IFM 140 are located at a position just distal of a transition portion of the strain relief member 134. However, it is contemplated that the channel 142 and the IFM 140 may be located at any position along the strain relief member 134.

FIGS. 6A-6J are cross-sectional views further illustrating alternative embodiments of the portion of a hub assembly, such as hub assembly 30/130, including an IFM, such as IFM 40/140. Although FIGS. 6A-6J refer to a portion of the hub assembly 30 identified in FIG. 3 as a portion of the manifold 32, the portion of the hub assembly having an IFM as illustrated in FIGS. 6A-6J may be located on any portion of a manifold, a strain relief member, or a proximal portion of the elongate shaft. FIG. 6A shows hub assembly portion 244 having a channel 242. Channel 242 is substantially flat-bottomed, but may take on a variety of shapes. The size and shape of the channel 242 is determined in order to accommodate IFM 240 and retain at least a portion therein. The IFM 240 is disposed about at least a portion of channel 242, wherein a portion of IFM 240 extends above the surface of portion 244 adjacent IFM 240. IFM 240 comprises a generally circular cross-section.

Figure 6B:
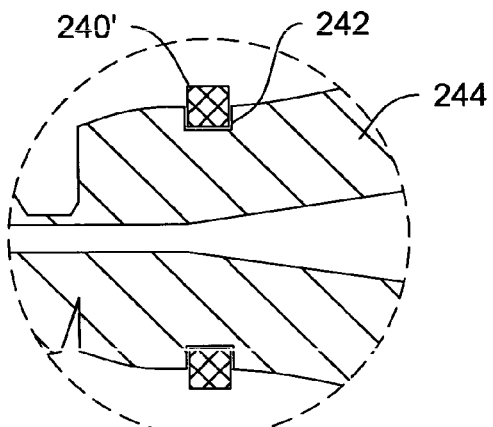
Figure 6C:
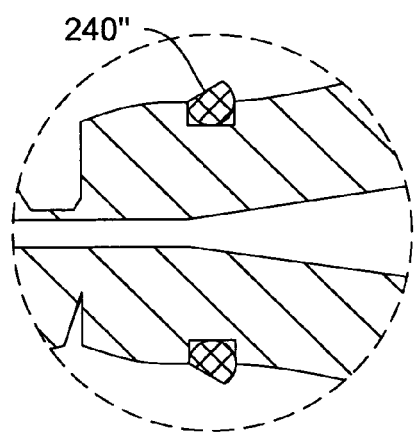
Figure 6D:
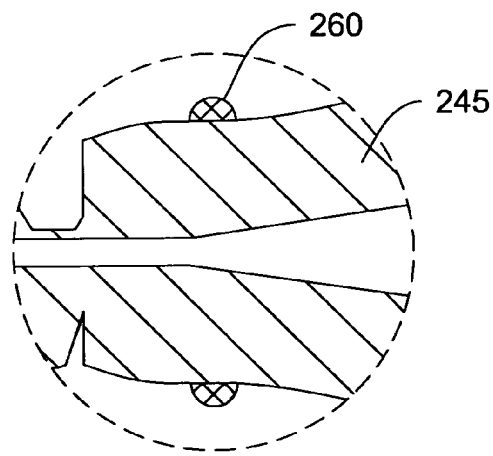

FIG. 6B shows a portion 244 having a channel 242. IFM 240' is disposed about the channel 242. IFM 240' is shown to have a square cross-section, but could also be substantially rectangular. FIG. 6C shows an alternative IFM 242" having a ramped portion to facilitate insertion in the packaging tube lumen 14. FIG. 6D shows a portion 245 without a channel or groove. IFM 260 may be a bead formed or placed about portion 245. IFM 260 may be a generally flowable or liquid substance which solidifies upon placement about portion 245, or IFM 260 may be solid member disposed about portion 245. IFM 260 may be adhered to the portion 245 with an adhesive, or IFM 260 may be adhered by chemical or thermal bonding means. IFM 260 creates a raised surface about portion 245 in order to contact the inner surface 16 of the packaging tube 10.

Figure 6E:
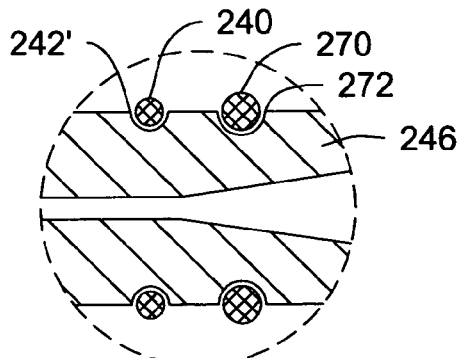
Figure 6F:
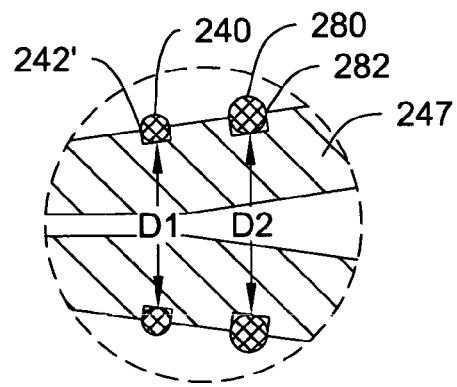

FIGS. 6E and 6F illustrate a portion of an elongate medical device having multiple IFMs. FIG. 6E shows a portion 246 having a channel 242' and channel 272. As illustrated in FIG. 6E, channels 242' and 272 may be concave channels. Channel 272 is shown to be larger than channel 242'. However channels 272/242' may be substantially the same size. IFM 240 is disposed about channel 242' and IFM 270 is disposed about channel 272. IFM 270 is shown to be larger than IFM 240, but IFMs 240/270 may be substantially the same size. IFMs 240/270 may be sized to accommodate packaging tubes 10 having lumens 14 of differing sizes. Therefore, IFM 270 would be configured to engage the inner surface 16 of a packaging tube 10 in which IFM 240 would not create an interference fit. This arrangement allows more versatility and compatibility between elongate medical devices and packaging tubes.

FIG. 6F shows a tapered portion 247 of an elongate medical device. The tapered portion 247 includes a plurality of channels 242/282. Channel 282 may be substantially different in size and/or shape from channel 242, or channels 242/282 may be substantially similar. IFM 240 is disposed about the channel 242, and IFM 280 is disposed about the channel 282. IFM 280 may be substantially different in size and/or shape from IFM 240, or IFMs 240/280 may be substantially similar. IFMs 240/280 and/or channels 242/282 may be sized to accommodate packaging tubes 10 having lumens 14 of differing sizes. IFMs 240/280 and/or channels 242/282 may also be sized to create differing degrees of interference with the inner surface 16 of a packaging tube 10. For example, the diameter D1 of channel 242 may be less than the diameter D2 of channel 282. This arrangement will provide IFM 280 with a larger outer diameter than IFM 240.

Figure 6G:
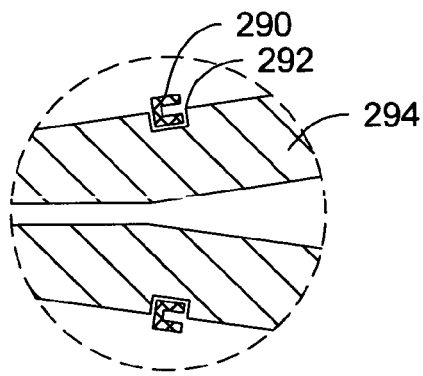
Figure 6H:
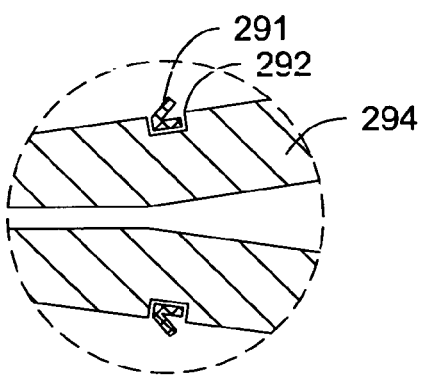

FIGS. 6G and 6H illustrate other embodiments of the invention. IFM 290, shown in FIG. 6G, may be a seal, such as a lip seal. IFM 290 may be disposed about portion 294. Portion 294 may include a channel 292, or portion 294 may comprise a substantially even surface. FIG. 6H shows IFM 291 similar to IFM 290. IFM 291 includes a ramped surface for engaging the inner surface 16 of a packaging tube 10. IFM 291 may be disposed about channel 292.

Figure 6I:
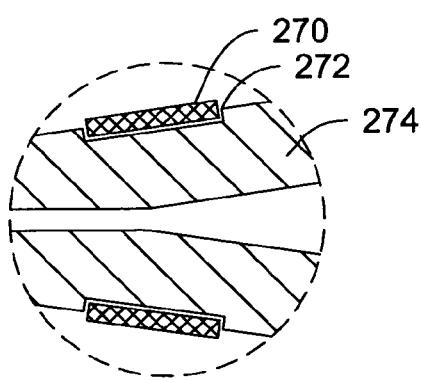

Referring to FIG. 6I, IFM 275 may be an elongated member. IFM 275 may be disposed about a tapered portion 274 of the elongate medical device. The tapered portion 274 may include an elongated channel 272 compatible for receiving at least a portion of the IFM 275. However, the tapered portion 274 may be formed without a channel. IFM 275 may be adhered to the tapered portion 274 by adhesive, chemical or thermal bonding means, or IFM 275 may not be adhered to the portion 274. IFM 275 may be elastically stretched about portion 274 in order to be compressively engaged with portion 274. IFM 275 may be made of a variety of materials suitable for engagement with the inner surface 16 of the packaging tube 10. The IFM 275 may have an outer circumference that varies along the length of the tapered portion 274. Therefore, the IFM 275 is compatible for providing an interference fit with a range of sizes of packaging tubes 10. Also, IFM 275 disposed about tapered portion 274 allows for varying degrees of interference between the tapered portion 274 and the inner surface 16 of the packaging tube 10. This arrangement allows for user-preferred variations of interference fits.

Figure 6J:
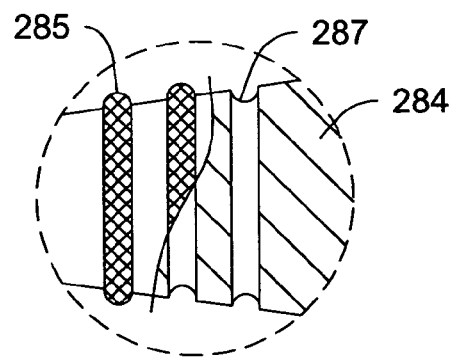

FIG. 6J shows yet another embodiment of the present invention. Tapered portion 284 includes a helical channel 287 extending along tapered portion 284. IFM 285 is disposed about the helical channel 287. IFM 285 disposed helically about the tapered portion 284 is compatible for providing an interference fit with a range of sizes of packaging tubes 10. Also, IFM 285 disposed about tapered portion 284 allows for varying degrees of interference between the tapered portion 284 and the inner surface 16 of the packaging tube 10.

Figure 7:
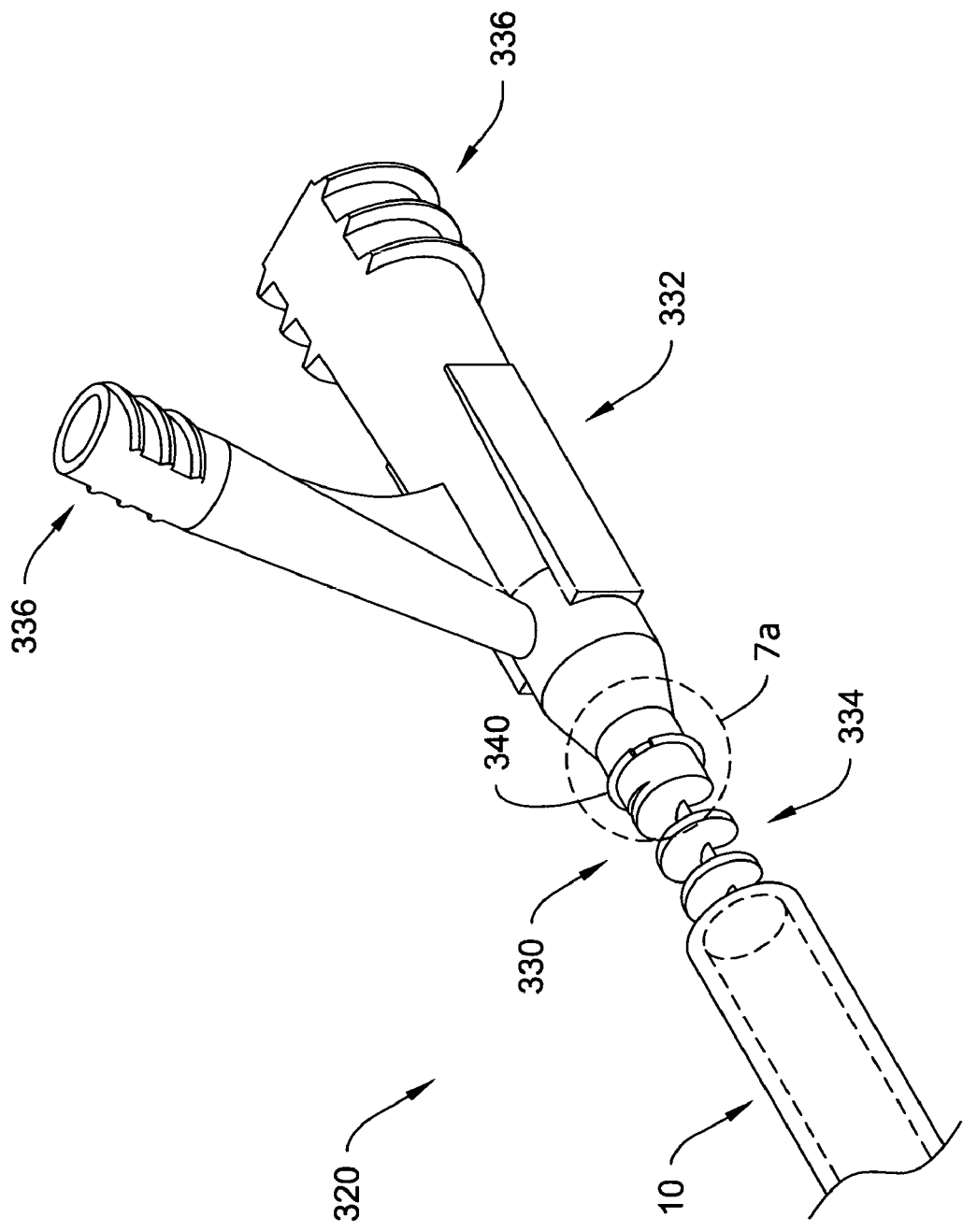
FIG. 7 is a perspective view of an alternative embodiment of an elongate medical device having an interference fit member in accordance with the invention.

Referring to FIG. 7, another embodiment of an elongate medical device 320 in accordance with the invention shows hub assembly 330 partially disposed in packaging tube 10. The hub assembly includes a manifold 332 and a strain relief member 334. The manifold 332 includes a plurality of proximal ports 336. An IFM 340 is disposed about a portion of the manifold 332. As is more clearly illustrated in FIG. 7A, a channel 342 is provided around a portion of the manifold 332 for receiving the IFM 340. As shown in FIG. 7B, IFM 340 comprises a ring having a gap 341. The ring may have a circular cross-section or any other suitable cross-section. The gap 341 allows for expandable and compressible movement deeper into the channel of the IFM 340. The IFM 340 may be expanded in order to be disposed about channel 342. Further, the IFM 340 may be compressed in order to be disposed within the lumen 14 of the packaging tube 10. The IFM 340 then will expand in order to attempt to return to its static form. In doing so, the IFM 340 will engage the inner surface 16 of the packaging tube 10, creating an interference fit. The biasing force of the IFM 340 may be varied depending on the size, shape, and material of the IFM 340.

Those skilled in the art will recognize that the present invention may be manifested in a variety of forms other than the specific embodiments described and contemplated herein. Variations and combinations of the invention not provided in the specific embodiments are held to be within the scope of the invention. Accordingly, departures in form and detail may be made without departing from the scope and spirit of the present invention as described in the appended claims.

What is claimed is:

1. An elongate medical device suitable for packaging in a generally tubular member having a lumen defined by an inner surface, the elongated medical device comprising:
   an elongate shaft having a proximal end and a distal end, the elongate shaft extending from a proximal portion of the elongated medical device to a distal portion of the elongated medical device;
   a hub assembly including a proximal end and a distal end, the proximal end of the elongate shaft connected to the hub assembly such that the elongate shaft extends distally from the distal end of the hub assembly, the hub assembly including at least a portion manufactured from a first material; and
   an interference fit structure including a second material helically disposed about at least a part of the portion of the hub assembly including the first material, the interference fit structure including a first portion having an outer diameter and a second portion having an outer diameter different from the outer diameter of the first portion, the first portion of the interference fit structure configured to contact and form an interference fit with an inner surface of a generally tubular member having a first inner diameter when the elongate shaft and the interference fit structure are disposed therein, and the second portion of the interference fit structure configured to contact and form an interference fit with an inner surface of a generally tubular member having a second inner diameter different from the first inner diameter when the elongate shaft and the interference fit structure are disposed therein.

2. The elongate medical device of claim 1, wherein the hub assembly further comprises:
   a distal portion including at least a segment having a generally circular cross-section including the first material; and
   a channel extending around the segment of the distal portion of the hub assembly including the first material, wherein at least a portion of the interference fit structure is disposed in the channel 3. The elongate medical device of claim 1, wherein the hub assembly further comprises:
   a manifold having a distal portion including the first material, wherein the interference fit structure is disposed about the distal portion of the manifold.

4. The elongate medical device of claim 3, wherein the hub assembly further comprises:
   a strain relief member, wherein the manifold and the strain relief member are integrally formed.

5. The elongate medical device of claim 1, wherein the hub assembly further comprises:
   a strain relief member, wherein the interference fit structure is disposed about the strain relief member.

6. The elongate medical device of claim 5, wherein the hub assembly further comprises:
   a manifold, wherein the strain relief member is affixed to the manifold.

7. The elongate medical device of claim 1, wherein the second material is more compressible than the first material.

8. The elongate medical device of claim 1, wherein the second material is readily deformable compared to the first material.

9. The elongate medical device of claim 1, wherein the second material is elastomeric.

10. The elongate medical device of claim 1, wherein the interference fit structure is disposed in a helical channel of the hub assembly.

11. An elongate medical device suitable for packaging in a generally tubular member, the generally tubular member having a lumen defined by an inner surface, the elongate medical device comprising:
    an elongate shaft having a proximal portion and a distal portion;
    a hub assembly including at least a portion manufactured from a first material, the hub assembly connected to the proximal portion of the elongate shaft such that the elongate shaft extends distally from the hub assembly, wherein the portion of the hub assembly manufactured from the first material includes a circumferential channel; and
    a circumferential interference fit member disposed in the circumferential channel, the circumferential interference fit member including a second material helically disposed about at least a part of the portion of the hub assembly including the first material;

wherein the circumferential interference fit member is configured to form an interference fit with the inner surface of the generally tubular member when the elongate shaft and the circumferential interference fit member are disposed in the lumen of the tubular member.

12. The elongate medical device of claim 11, wherein the hub assembly further comprises:
   a manifold having a distal portion including the first material, wherein the circumferential interference fit member is disposed about the distal portion of the manifold.

13. The elongate medical device of claim 12, wherein the hub assembly further comprises:
   a strain relief member, wherein the manifold and the strain relief member are integrally formed.

14. The elongate medical device of claim 11, wherein the hub assembly further comprises:
   a strain relief member, wherein the circumferential interference fit member is disposed about the strain relief member.

15. The elongate medical device of claim 14, wherein the hub assembly further comprises:
   a manifold, wherein the strain relief member is affixed to the manifold.

16. An elongate medical device packaging assembly comprising:
   a generally tubular packaging member having a proximal end, a distal end and a lumen defined by an inner surface;
   a hub assembly including a proximal end and a distal end, the hub assembly including at least a portion manufactured from a first material;
   an elongate shaft having a proximal end and a distal end, the proximal end of the elongate shaft being connected to the hub assembly such that the elongate shaft extends distally from the distal end of the hub assembly; and
   an interference fit member including a second material helically disposed about at least a part of the portion of the hub assembly including the first material;
   wherein the elongate shaft and at least a distal portion of the hub assembly are disposed in the lumen of the generally tubular packaging member such that the interference fit member is engaged with the inner surface of the generally tubular packaging member to form an interference fit with the inner surface of the generally tubular packaging member.

17. The elongate medical device packaging assembly of claim 16, wherein the interference fit member is helically disposed about a tapered portion of the hub assembly.

* * * * *